United States Patent [19]

Lippman

[11] Patent Number: 5,034,176

[45] Date of Patent: Jul. 23, 1991

[54] METHOD OF MAKING A PLASTIC ARTICLE HAVING A PLURALITY OF TINY, THROUGH OPENINGS

[76] Inventor: Myron E. Lippman, 824 Alston Rd., Santa Barbara, Calif. 93108

[21] Appl. No.: 472,210

[22] Filed: Jan. 29, 1990

[51] Int. Cl.$^5$ .................... B29C 51/02; B29C 55/22
[52] U.S. Cl. .................... 264/157; 264/221; 264/225; 264/291; 264/344; 264/317; 264/164
[58] Field of Search .......... 264/171, 164, 288.4, 264/290.5, 291, 157, 241, 225, 317, 221, 349, 344; 65/3.13, 23

[56] References Cited

U.S. PATENT DOCUMENTS

| | | | |
|---|---|---|---|
| 1,713,679 | 5/1929 | Snelling | 264/173 |
| 2,030,208 | 2/1936 | Harrison | 264/166 |
| 2,414,226 | 1/1947 | Everett | 264/317 |
| 2,875,501 | 3/1959 | Gravley | 264/173 |
| 3,099,067 | 7/1963 | Merriam | 264/166 |
| 3,350,488 | 10/1967 | Breen | 264/344 |
| 3,382,305 | 5/1968 | Breen | 264/171 |
| 3,486,868 | 12/1969 | Goodrich | 264/317 |
| 3,549,734 | 12/1970 | Yasuda | 264/349 |
| 3,562,374 | 2/1971 | Okamoto | 264/344 |
| 3,716,614 | 2/1973 | Okamoto | 264/344 |
| 4,034,751 | 7/1977 | Hung | 264/173 |
| 4,070,514 | 1/1978 | Eatherly | 264/317 |
| 4,250,127 | 2/1981 | Warren | 264/317 |

OTHER PUBLICATIONS

"New Regulator Used for Intractable Glaucoma", Ophthalmology Times; vol. 15, No. 14, Jul. 15, 1990.

*Primary Examiner*—Jay H. Woo
*Assistant Examiner*—Jeremiah F. Durkin, II
*Attorney, Agent, or Firm*—Jack C. Munro

[57] ABSTRACT

The method of making a plastic article having a plurality of small openings which utilizes a plurality of thin plastic tubular members combined together in a side-by-side relationship forming an assemblage. Each tubular member has an exterior layer of a first plastic and a core of a second plastic. The second plastic is to be dissolvable by a solvent. This assemblage is passed through a furnace with the result that the assemblage is drawn into a thin filament. Once cooled, the thin filament is cut into segments of a desired length and these segments are placed within a solvent bath for a sufficient period of time in order to affect complete removal of the second type of plastic resulting in producing of a plurality of small, through openings within each section.

5 Claims, 1 Drawing Sheet

METHOD OF MAKING A PLASTIC ARTICLE HAVING A PLURALITY OF TINY, THROUGH OPENINGS

BACKGROUND OF THE INVENTION

The field of this invention relates to the locating of one or more tiny holes within a block of material and principally to the locating of the holes within a block of plastic.

The subject matter of the present invention is to be discussed in conjunction with the field of medicine. However, it is to be understood that the subject matter of this invention could be utilized in numerous other fields, many of which may even be unknown to the inventor. The contemplated field of utility of this invention is directed to obtaining of an orifice member which provides for a restricted flow of a liquid through this orifice member. This restriction of flow can be of particular advantage within the medical field or within any other field where a restricted flow would be desirable.

In the constructing of any liquid conducting orifice, the side wall of the orifice would frictionally resist the flow of the liquid through the orifice. Normally, it is the intention to decrease this restriction so that the liquid can flow through the orifice with the minimum amount of resistance, therefore, a minimal amount of energy loss. However, this restriction to the flow of a liquid through an orifice can be utilized to advantage in certain environments.

The smaller the orifice, the greater the restriction. Also, the longer the orifice, the greater the restriction. If the orifice size is a thousandth of an inch or less, and the orifice separates a pair of fluid mediums with one fluid medium being at a pressure differential greater than the other, then that restriction could be utilized to maintain a certain pressure differential relationship between the two fluid mediums. There is a problem with a single orifice in that not much flow is permitted. Therefore, it is common to utilize a mass of orifices, all of which have the same size and which have the same amount of restriction. It is this mass of orifices that more effectively control and maintain the established pressure differential.

Within the field of medicine, a common disease in conjunction with eyes is glaucoma. Within the eyeball is located a liquid. This liquid is under pressure with a common pressure being approximately twenty millimeters of mercury. In glaucoma, this pressure increases and if the pressure gets too severe, the patient can actually go blind.

In the past, there have been different techniques in order to relieve this excessive pressure. A vast amount of money is spent each year on drops that are to be placed onto the eye that are minimally effective. Additionally, there have been numerous surgical techniques in order to relieve this pressure. One of the most common surgical techniques is merely to cut a hole into the eyeball which provides an outlet for some of the liquid contained in the eyeball thereby relieving the pressure. This hole is then sutured. The disadvantage of this technique is that initially the pressure of the liquid in the eyeball is decreased below the desired level to atmospheric pressure. As time goes on, the pressure will again build up back to its original level which will require a duplicating of the surgical technique.

To overcome the disadvantage of this technique, there has been manufactured a valve assembly which is to be mounted in conjunction with the eyeball and located within the hole cut into the eyeball. It is the function of the valve to be activated if a certain pressure level is exceeded and provide an escape route for some of the liquid contained within the eyeball thereby releasing the pressure. The disadvantage to this valve is that it frequently malfunctions thereby requiring replacement or complete removal of this valve unit.

Another known device has to do with utilizing a balloon operating pump as opposed to a valve. This balloon operated pump is to release liquid when the pressure is applied to the balloon. This pressure is to be applied by the natural blinking process of a human being or is to be applied by manual rubbing of one's eye. However, the patient is not sensitive to increased eye pressure, therefore, is not able to determine when it is desirable to operate the pump. Again, this type of unit is not free from malfunction although, prior to the present invention, is probably the best device available to relieve accumulated liquid pressure from the interior of an eyeball.

The present inventor discovered that if a tiny block of plastic could be manufactured with a mass of tiny, through openings, and this block of material was installed in conjunction with a hole extending into the interior of an eyeball, that depending on the size of these openings, a pressure differential can be established between the interior of the eyeball and the ambient which could be maintained without utilizing any moving parts. By varying the size of these holes, this pressure differential could also be varied. As the pressure increases, the amount of flow through the orifices increases, thereby decreasing the pressure. This is a desirable feature since not all people have the same liquid pressure within the interior of the eyeball. Therefore, if the size of the orifices could be precisely controlled, a custom designed liquid relief passage arrangement could be manufactured for that particular individual. The liquid that is conducted from the interior of the eyeball to the exterior of the eyeball is discharged naturally through the waste disposal system of the human being.

It has been impossible in the past to manufacture a block of material which had a mass of precisely sized, tiny openings. Small openings can be formed within a block of material, such as plastic, by the utilizing of a laser. However, lasers cannot, at present, make the openings that are required by the present invention as the minimal size of opening that can be formed by the laser is still too large or not of sufficient length. Therefore, another method had to be arrived at to manufacture such small openings of adequate length.

It is to be reiterated that the method of the present invention can be used to manufacture articles which are usable in other fields of endeavor. One example would be in the making of contact lenses for the eye. One of the inherent problems of a contact lens is that liquid and oxygen is normally blocked by the lens so there is no way for fluid from the exterior surface of the eyeball to penetrate to the interior surface of the lens. If a lens was manufactured in accordance with the method of the present invention, there would be a mass of tiny holes, or through openings, formed within the lens which would permit this liquid and oxygen to be conducted to the interior surface of the lens. This mass of tiny holes would not interfere with the normal vision of the lens.

SUMMARY OF THE INVENTION

The method of making a plastic article which has a plurality of small, through openings. This method has to do with the forming of an enlarged, elongated, tubular bar which is substantially hollow with this bar being constructed of a first type of plastic that is not dissolvable by a solvent. Within the hollow is located a second type of plastic that is dissolvable by a solvent. This bar is conducted vertically from an elevated position to a lowered position through a furnace which causes the lower end of the bar to melt and be drawn into a thin, elongated tubular member having a cross-sectional area less than the cross-sectional area of the bar while maintaining substantially the same proportion of first plastic to the second plastic as was contained within the bar. Sections of this tubular member are produced to a given length. A quantity of these tubular members are located in juxtaposition and bound together forming an assemblage. This assemblage is then conducted through the furnace in the manner previously described resulting in producing of a thin filament having a plurality of internally located threads of the second type of plastic. This filament is then to be cut into desired lengths and placed within a solvent bath for a period of time, sufficient to dissolve the second type of plastic producing a plurality of spaced apart small, through openings within this filament.

The primary objective of the present invention is to provide a method which permits the forming of tiny, through openings within a block of plastic material with the size of these openings being so small that they are not capable of being manufactured by any known prior art technique.

Another objective of the present invention is to utilize a method which provides for obtaining of a precise size of opening and capable of precisely varying the size of opening within a block of plastic material.

Another objective of the present invention is to provide for a method which permits relatively inexpensive manufacture of products with precisely sized, tiny openings within a plastic block of material.

DETAILED DESCRIPTION OF THE INVENTION

Figure 1:
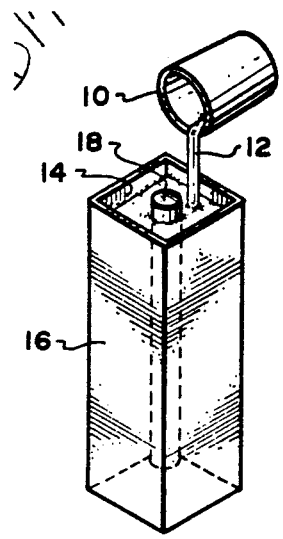
FIG. 1 schematically depicts a portion of the method of this invention which is used to construct the elongated tubular bar of the first type of plastic with this bar being hollow.
Figure 2:
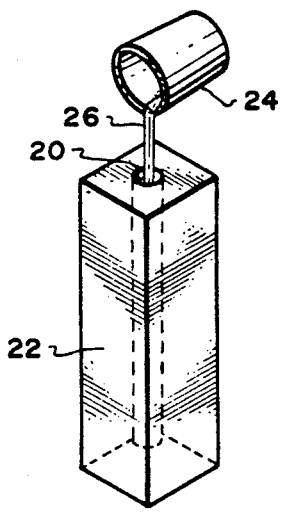
FIG. 2 is a view similar to FIG. 1 but showing the filling of the hollow with a second type of plastic and this second type of plastic being dissolvable by a solvent.
Figures 3, 4:
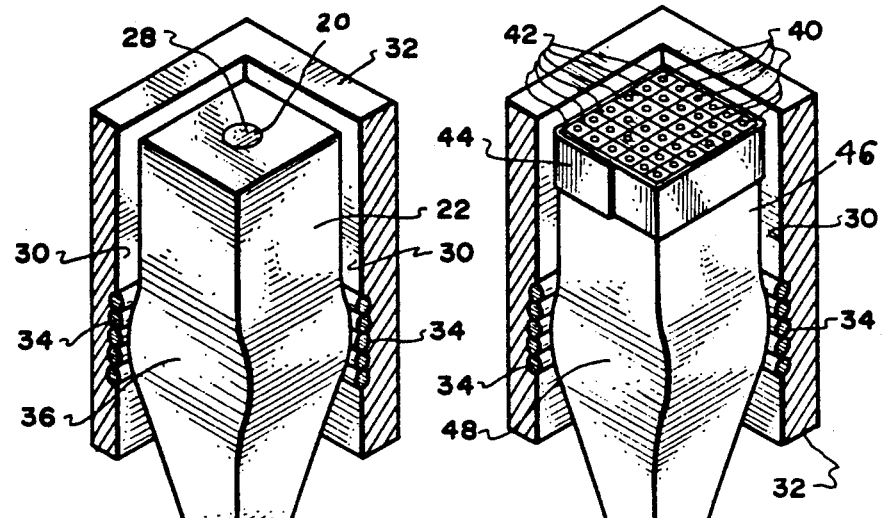
FIG. 3 is a partly cross-sectional view depicting movement of the bar within a furnace which will cause the bar to be drawn into a substantially decreased cross-sectional area while yet maintaining in proportion and location cross-sectionally the amount of the first plastic and the second plastic.
FIG. 4 is a view similar to FIG. 3 depicting the forming into a thin filament by an assembled arrangement of the thin tubular members produced by the procedure within FIG. 3.
Figure 5:
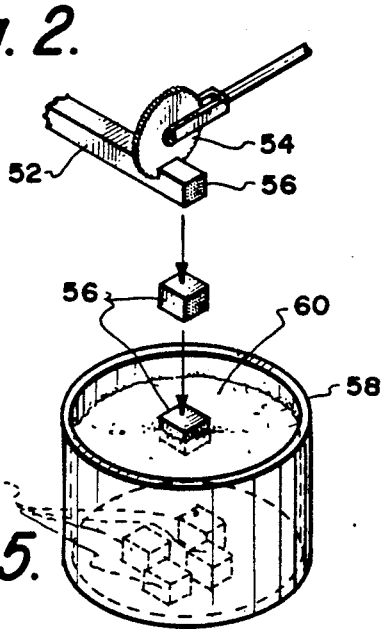
FIG. 5 is a view depicting the cutting of the filament produced within the FIG. 4 into desired lengths and inserting such within a solvent bath for the removal of the threads of second plastic which are laced through the now formed block.
Figure 6:
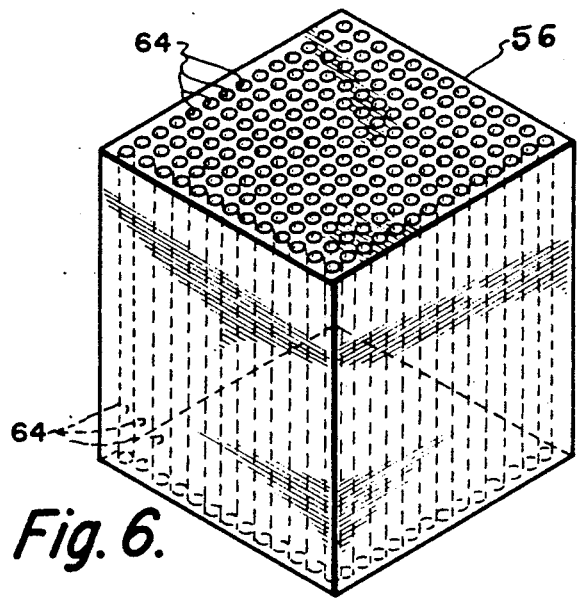
FIG. 6 is an isometric view of the plastic article which has been produced in accordance with the method of this invention.

Within the drawing, there is generally depicted the method of the present invention. It is to be understood that the drawing only gives a generalized representation of the procedure of the method of this invention and that in actual practice the structure that is to effect the method of this invention may be different than what is actually shown.

There are two different plastics, generally, that will be utilized. Common types of plastics that have been found to preferable would be a polymethyl methacrylate and polystyrene. Polymethyl methacrylate would probably be the preferable material for the reason that this material has been found to be an acceptable material within the medical field and would not require any material approval by any federal agency. However, it is considered to be within the scope of this invention that other material could be utilized without departing from the scope of this invention.

Of the two different plastics that are utilized, both could comprise polymethyl methacrylate. One of the polymethyl methacrylates would not be dissolvable by a solvent, with the other polymethyl methacrylate being dissolvable by a solvent. For the purpose of this invention, the plastic not dissolvable will be referred to as the first plastic and the plastic that is dissolvable by a solvent will be referred to as a second plastic.

Both the first and second plastics will have substantially identical melting points somewhere in the range of three hundred thirty degrees Fahrenheit to three hundred ninety degrees Fahrenheit. It is important that the second plastic have a melting point no greater than the first plastic. Actually, it would probably be preferable that the second plastic have a slightly less melting point than the first plastic for a reason which will become apparent further on in this specification.

The first plastic will normally come in the initial form of a mass of pellets (not shown). These pellets will be melted within a vessel 10 forming a liquid plastic 12. This liquid plastic 12 is poured into an internal chamber 14 of a mold 16. The mold 16 includes a center tube 18 which will result into the forming of a hollow cylindrical shaped hole 20 of the resultingly formed plastic bar 22 when it is removed from the mold 16. It is to be understood that, normally, the mold 16 will be placed within an injection molding machine (not shown). It is preferable that the transverse cross-sectional configuration of the bar 22 be square with the hollow 20 being circular. However, it is considered to be within the scope of this invention that the bar 22 could be another polygonal configuration, or could be a non-polygonal configuration, such as cylindrical. Generally, the length of the bar 22 is one and one-half to two feet long and being one and one-half to three inches square. The diameter of the hole 20 will normally be between one inch to one and one-half inches.

When the bar 22 has been removed from mold 16 it is permitted to cool to room temperature. It is desirable to insure that any gas and moisture that has become impregnated in the bar 22 be released. The reason for this is that gas and/or moisture will cause producing of a rejectable product. Also, at times, in the molding procedure, there may be produced a certain amount of stress within the bar 22 and it is desirable to remove this stress. In order to remove the gas, moisture and stress, the bar 22 is placed within a vacuum chamber (not shown) with a slight vacuum, such as twenty-nine inches of mercury being pulled on the bar 22. This bar 22 is stored within this chamber, which is heated to approximately two hundred fifty degrees Fahrenheit, for a certain length of time such as twenty-four hours. This procedure is to be described as THERMOVAC throughout the specification of this invention.

After the twenty-four hour period, the bar 22 is removed from the THERMOVAC chamber and permitted to again cool to room temperature. At this particular time, a quantity of the second plastic is heated within heating vessel 24 and liquefied into a liquid plastic 26. This liquid plastic is then poured into the hollow 20. Normally, this pouring into hollow 20 will be completed within an injection molding machine in order to insure the side walls of the bar 22 do not bow in an outward direction because of the application of the heat from the second plastic 26. Once the liquid second plastic 26 is cooled into a solid plastic 28, the bar 22 is then placed again within the THERMOVAC chamber for a twenty-four hour period.

After the bar 22 has been removed from the THERMOVAC chamber and cooled, it is suspended in a vertically oriented manner by an appropriate overhead suspension mechanism (not shown). The bar 22 is to be located in an elevated position. Vertically oriented means one end of the bar 22 is located directly above and in alignment with the opposite end of the bar 22 and the longitudinal center axis of the bar 22 is in alignment with the direction of the gravity force on the bar 22.

The bar 22 is then to be moved into the through opening 30 of a furnace 32. The lower portion of this furnace 32 includes a heating coil assembly 34. When the lower end of the bar 22 become located directly adjacent the coil 34, the heat will be sufficient to cause expansion of the bar 22 forming an expanded section 36. Melting of the entire cross-sectional area of the bar 22 is to occur. Bar 22 is then drawn into a substantially decreased cross-sectional size tubular member 38. Centrally disposed within this tubular member 38 is a core 40. In cross-section, the proportional size of the core 40 to the overall cross-section of the tubular member 38 is maintained the same as the relationship of hollow 20 to bar 22. It is to be understood that the core 40 is actually hollow 20 but in a small diameter. Each core 40 is filled with second plastic 28. The tubular member 38 is then to be cut into prescribed lengths such as two foot lengths 42.

The lengths 42 are again cooled and then placed within the THERMOVAC chamber for a period of time, such as four hours. A quantity of the lengths 42 are to be assembled together in juxtaposition, secured at the ends by means of a tape-like band 44 forming an assemblage 46. The assemblage 46 is basically the same size and of a square configuration as bar 22. This assemblage 46 is then again placed within the THERMOVAC chamber. The temperature at this time within the THERMOVAC chamber is increased to be just below the melting point of the plastics which will result in the tubular members 42 slightly melting together thereby bonding the assemblage 46 into a single unit. The assemblage 46 is then removed from the THERMOVAC chamber and permitted to cool. At this particular time, the bands 44 could be removed if such is deemed to be desired.

The assemblage 46 is mounted in the same manner as bar 22 was mounted in conjunction with the furnace 32. Assemblage 46 is moved through the chamber 30 of the furnace 32 with the lower end of the assemblage 46 being melted by being located directly adjacent the heating coil 34. The assemblage 46 will assume an expanded section 48 prior to being drawn into a thin filament 50. The thin filament 50 will be cut into desired lengths 52, such as a two foot length. The length 52 is to be cut by means of a cutting blade 54 into a mass of small blocks 56. Prior to being cut into the blocks 56, the filaments 52 will normally be placed in the THERMOVAC chamber again for a short period of time such as four hours. Prior to being cut into the blocks 56, the filaments 52 are to be cooled to room temperature.

The size of the blocks 56 can be any desired length. A preferable size is one-sixteenth to one-eighth inch long when used in conjunction with a device that will ultimately be mounted to treat glaucoma. Blocks 56 will actually be polished in bulk to eliminate any burrs and sharp corners prior to being deposited within reservoir 58 which contains a solvent 60. A desirable solvent 60 could be any liquid which would remove the now formed mass of threads of second plastic that extend through each block 56. Each thread is actually a smaller diametered section of second plastic 28 which is contained within the smaller diametered cores 40. A typical solvent would be within the group of xylene, trichloroethylene, acetone, methyl ethyl ketone, and methylene chloride. However, it is considered to be within the scope of this invention that other solvents could possibly be utilized. Generally, the length of time within the solvent reservoir 58 would be between five minutes to two hours.

After the submersion of the blocks 56 within the reservoir 58 which contains the solvent 60, the blocks 56 are removed and permitted to dry. The resultingly formed block 56 includes a plurality of evenly spaced apart, through openings 64, small in cross-section, which were actually cores 40. In essence, these openings 64 resemble a mass of threads formed within the blocks 62. The cross-sectional size of each of the openings 64 will generally be one-thousandth of an inch or less. The actual size of the opening 64 can be controlled by the cross-sectional thinness of the filament 52 that is produced. It is to be kept in mind that the proportional size of each of the cores 40 of each tubular member 42 is maintained in conjunction with the filament 52. So, therefore, the thinner the filament 52 that is produced, the smaller the block 62 and, hence, smaller the opening 64. It is not at all uncommon to produce two hundred twenty-five openings 64 within an eighth inch square block 62.

It is envisioned that different techniques could be utilized to eliminate the core plastic 40. Possibly, by utilizing a slightly different melting temperature for the core plastic 40 relative to the first plastic, and by carefully raising of the temperature of each of the blocks 56 that the core plastic can be eliminated by melting leaving intact the remaining portion of the block 56 thereby producing the block 62. At the present time, there is no known method to produce such small, through openings 64 by physically cutting either by drilling or by a laser.

What is claimed is:

1. The method of making a pressure relief device to be inserted in an eyeball, said device including a plastic article with a plurality of small, parallel, through openings, said method comprising the steps of:
- forming an enlarged, elongated, tubular bar being hollow substantially along its entire longitudinal length defining an interior chamber, said bar being constructed of a first plastic, said first plastic being insoluble by a solvent;
- filling said interior chamber with a second plastic forming a core, said second plastic being soluble by a solvent; and
- moving said tubular bar vertically from an elevated position to a lowered position through a furnace causing the lower end of said bar to melt and be drawn into a tubular member having a cross-sectional area substantially less than the cross-sectional area of said bar while maintaining substantially the portion of said first plastic to said second plastic as was contained within said bar,
- combining a plurality of said tubular members in juxtaposition forming an assemblage with said cores being parallel and straight;
- binding together said assemblage;
- moving said assemblage in a direction parallel to the longitudinal axis of said assemblage vertically from an elevated position to a lowered position through a furnace causing the lower end of said assemblage to melt and extend from said furnace and be drawn into a filament having a cross-sectional area substantially less than the cross-sectional area of said assemblage resulting in said cores of said filament forming a plurality of internally located threads of said second type of plastic;
- transversely cutting said filament into a plurality of substantially equal length segments; and
- removing said threads of each said segment by submerging said segments into a solvent leaving a plurality of spaced apart, small, parallel through openings each of which has a diameter of one thousandth of an inch or less.

2. The method as defined in claim 1 wherein:
the utilizing step includes selecting said second type of plastic to be dissolvable by a solvent.

3. The method of making a plastic article as defined in claim 2 wherein:
the removing step includes utilizing a solvent from the group consisting of xylene, trichloroethlyene, acetone, methyl ethyl ketone and methylene chloride.

4. The method of making a plastic article as defined in claim 1 wherein the utilizing step includes:
forming said plastic tubular member in a polygonal exterior configuration.

5. The method of making plastic article as defined in claim 1 wherein the binding step includes:
a slight melting together of said tubular members in the forming of said assemblage.

* * * * *